United States Defensive Publication [19] (H) [11] T102,303

Morrow [43] Oct. 5, 1982

[54] 5,6,7,8-TETRAHYDROTRIAZOLO{4,3-ALPHA}-PYRIDIN-3(2H)-ONES

[76] Inventor: Duane F. Morrow, 8200 Berry Dr., Evansville, Ind. 47710

[21] Appl. No.: 271,296

[22] Filed: Jun. 8, 1981

[51] Int. Cl.[3] ..... C07D 403/06

[52] U.S. Cl. ..... 544/362; 424/250

[57] ABSTRACT

5,6,7,8-Tetrahydrotriazolo{4,3-a}pyridin-3(2H)-one derivatives containing a 4-(optionally substituted phenyl)piperazinyl component attached to the 2- position of the tetrahydrotriazolo{4,3-a}pyridinone component via an alkylene chain of 3 or 4 carbon atoms are disclosed. Examples are compounds having the formula

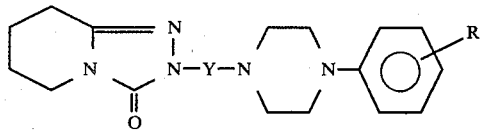

wherein R is lower alkyl or alkoxy (each having 1 to 4 carbon atoms inclusive), cyano, halogen, or trifluoromethyl; and Y is an alkylene chain of 3 or 4 carbon atoms. The compound in which R is 3-Cl and Y is trimethylene exhibits central nervous system pharmacological properties in standard laboratory tests which are predictive of useful anti-psychotic, antidepressant, and antianxiety action.

2 Claims, No Sheets Drawing,

10 Pages Specification

The file of this unexamined application may be inspected and copies thereof may be purchased (849 O.G. 1221, Apr. 9, 1968).